(12) United States Patent
Jang (10) Patent No.: US 10,971,268 B2
(45) Date of Patent: Apr. 6, 2021

(54) METHOD OF PROVIDING INFORMATION FOR THE DIAGNOSIS OF PANCREATIC CANCER USING BAYESIAN NETWORK BASED ON ARTIFICIAL INTELLIGENCE, COMPUTER PROGRAM, AND COMPUTER-READABLE RECORDING MEDIA USING THE SAME

(71) Applicant: Gumi Electronics & Information Technology Research Institute, Gumi-si (KR)

(72) Inventor: Ik-Gyu Jang, Gumi-si (KR)

(73) Assignee: GUMI ELECTRONICS & INFORMATION TECHNOLOGY RESEARCH INSTITUTE, Gumi-Si (KR)

( * ) Notice: Subject to any disclaimer, the term of this patent is extended or adjusted under 35 U.S.C. 154(b) by 791 days.

(21) Appl. No.: 15/833,828

(22) Filed: Dec. 6, 2017

(65) Prior Publication Data
US 2019/0035504 A1    Jan. 31, 2019

(30) Foreign Application Priority Data

Jul. 26, 2017    (KR) .................. 10-2017-0094700

(51) Int. Cl.
*G06N 5/04*    (2006.01)
*G16H 50/20*    (2018.01)
(Continued)

(52) U.S. Cl.
CPC ............ *G16H 50/20* (2018.01); *G06N 7/005* (2013.01); *G06N 20/00* (2019.01); *G16H 70/60* (2018.01); *G06N 3/08* (2013.01); *G06N 5/04* (2013.01)

(58) Field of Classification Search
None
See application file for complete search history.

(56) References Cited

FOREIGN PATENT DOCUMENTS

| KR | 10-2010-0062439 A | 6/2010 |
| KR | 10-2013-0100096 A | 9/2013 |

(Continued)

OTHER PUBLICATIONS

Naia, et al., How Early Can Pancreatic Cancer Be Recognized? A Case Report and Review of the Literature, Case Rep Oncol., 2015, pp. 46-49 (Year: 2015).*

(Continued)

*Primary Examiner* — Wilbert L Starks
(74) *Attorney, Agent, or Firm* — Lewis Roca Rothgerber Christie LLP (57) ABSTRACT

The present invention provides a method of providing information necessary for diagnosing pancreatic cancer using an artificial intelligence-based Bayesian network, comprising: generating a statistical report by learning medical information of a pancreatic cancer patient; constructing a conditional probability table using statistics for each symptom of an actual pancreatic cancer patient; constructing a Bayesian network using the conditional probability table constructed using the statistics for each symptom; applying a Bayesian conditional probability to the Bayesian network; and deriving a probability of getting pancreatic cancer when there is a specific symptom from the pancreatic cancer patient, wherein medical information on pancreatic cancer patients may be statistical data obtained through artificial intelligence or machine learning.

6 Claims, 4 Drawing Sheets

(51) Int. Cl.
  *G06N 7/00* (2006.01)
  *G06N 20/00* (2019.01)
  *G16H 70/60* (2018.01)
  *G06N 3/08* (2006.01)

(56) References Cited

FOREIGN PATENT DOCUMENTS

| | | |
|---|---|---|
| KR | 10-2016-0057352 A | 5/2016 |
| KR | 10-2017-0058391 A | 5/2017 |

OTHER PUBLICATIONS

Zhao, et al., Combining PubMed Knowledge and EHR Data to Develop a Weighted Bayesian Network for Pancreatic Cancer Prediction, Journal of Biomedical Informatics 44, 2011, pp. 859-868 (Year: 2011).*

Jang, I.G. et al.; "Intelligent Diagnosing Method for Pancreatic Cancer Early Detection"; Published in conference on the 16th International Conference on Biomedical Engineering on Dec. 7, 2016, 1pg.

* cited by examiner

METHOD OF PROVIDING INFORMATION FOR THE DIAGNOSIS OF PANCREATIC CANCER USING BAYESIAN NETWORK BASED ON ARTIFICIAL INTELLIGENCE, COMPUTER PROGRAM, AND COMPUTER-READABLE RECORDING MEDIA USING THE SAME

CROSS-REFERENCE TO RELATED APPLICATION

This application claims priority to Korean Patent Application No. 10-2017-0094700 filed on Jul. 26, 2017 and all the benefits accruing therefrom under 35 U.S.C. § 119, the contents of which is incorporated by reference in its entirety.

BACKGROUND OF THE INVENTION

1. Field of the Invention

The present disclosure relates to a method of providing information necessary for diagnosing pancreatic cancer using an artificial intelligence-based Bayesian network. More particularly, the present disclosure relates to a method of providing information, a computer program, and a computer-readable recording medium necessary for diagnosing pancreatic cancer using Bayesian conditional probability of an artificial intelligence-based Bayesian network, for diagnosing pancreatic cancer which is known to have a poor prognosis.

2. Description of the Related Art

The pancreas is a digestive and secretory organ in the body, attached to the lower gallbladder above the stomach.

The pancreas is an endocrine gland that carries out the secretion of pancreatic fats and hormones, such as insulin and glucagon, to regulate blood sugar levels regularly.

The pancreas is located in the deepest part of the body, surrounded by organs such as the duodenum and small intestine, located in the upper part of the upper abdomen of the human body, behind the stomach, and in the vertebrae.

In other words, diseases that occur in the pancreas are highly difficult to detect, mostly due to having almost no early symptoms, but also because the pancreas itself is surrounded by other organs.

In particular, early diagnosis is recommended for pancreatic cancer because the prognosis is extremely poor, and the mortality rate is high when symptoms are found.

That is, if relatively minor suspicious symptoms appear, it is advisable to perform an early screening or examination immediately.

However, even if it is simply suspected, it is only a subjective judgment, so it is necessary to objectively standardize the possibility of pancreatic cancer, and to diagnose pancreatic cancer in a smart way.

Currently known methods of early diagnosis of pancreatic cancer include blood tests, ultrasonography, computed tomography (CT), biopsy, and serum tumor markers.

Of these, the blood test cannot diagnose pancreatic cancer immediately. This is because the numerical value of some test results is in some cases similar to that of other diseases, so it is difficult to diagnose pancreatic cancer quickly and accurately at present.

Ultrasonography may be performed by abdominal ultrasonography or endoscopic ultrasonography (EUS). However, abdominal ultrasonography is not as accurate as early diagnosis, and endoscopic ultrasonography is known to be highly accurate, but its procedures and methods are somewhat tricky and generally difficult to use.

In addition, biopsy can be performed in cases of pancreatic nodules or pancreatic cancer, and it is used to determine the stage. However, this procedure is also somewhat difficult to use because the procedures and methods necessary for diagnosis are rather complicated.

Although Computed tomography (CT) examination is excellent in that they can be diagnosed by non-surgical treatment, it is disadvantageous in terms of time required for diagnosis and mass diagnosis.

On the other hand, the serum tumor marker test is a method for diagnosing pancreatic cancer by detecting a tumor marker, which is a substance that is specifically made by tumor cells and is an indicator for diagnosis or progress of cancer. And the most widely used tumor marker is CA (also known as Carbohydrate Antigen or Cancer Antigen) 19-9.

Tumor markers can be detected from other cancers of the digestive system, including bile ducts, other than pancreatic cancer. However, serum tumor markers can be a diagnosis in the future because of simple procedures for diagnosis, low cost, and mass diagnosis.

The CA 19-9 cancer marker was presented in 1981 as a pancreatic cancer marker, isolated from the serum of patients with colon cancer and pancreatic cancer, from the American Institute of Anatomy and Biology, Covellowski.

The pancreatic cancer margin of a specific patient can be determined by examining the values obtained by spectrophotometry using chemiluminescence techniques that respond to specific antibodies (i.e. CA 19-9 cancer markers) contained in the patient's blood.

Currently, there is SelexOn™ for immunoassays released from Infopia as a commercially available product using CA 19-9 cancer markers in Korea.

The product can diagnose not only cancer-related diseases such as pancreatic cancer but also other heart-related diseases with only a very small amount of blood. Since the time required for diagnosis is also about 10 minutes, if the concept of not only post-onset but also pre-emergence prevention is taken into consideration, it is expected to be a very efficient product. Also this product can be used to determine the prognosis of pancreatic cancer and to obtain the indicators needed for follow-up after treatment.

However, CA 19-9 cancer markers generally have a sensitivity of 79 to 81% for patients with pancreatic cancer, and False-Positive results for patients with symptoms such as pancreatitis or jaundice, it is not recommended as a single criterion for screening.

In particular, the American Society of Clinical Oncology (ASCO) does not recommend the use of CA 19-9 cancer markers as a screening test for pancreatic carcinoma because of the False-Positive, but CA19-9 cancer markers are recommended only for patients with pancreatic tumors to distinguish pancreatic cancer from other diseases.

Therefore, there is a need for a method that can increase the accuracy/sensitivity of discrimination for pancreatic cancer, while using CA 19-9 cancer markers that are simple, rapid and can be treated in massive amounts.

In the prior art known in the art to which the present invention belongs, the possibility of developing pancreatic cancer is determined by using a composition for diagnosing pancreatic cancer including a marker protein for diagnosis of pancreatic cancer including CA 19-9 (carbohydrate antigen 19-9) and the like (see Patent Document 1).

However, as described above, CA 19-9 cancer markers are not free from the False-Positives, which is a problem that cannot be avoided in Patent Document 1 as well.

Therefore, in consideration of the circumstances of the occasion, the inventors of the present invention used existing CA 19-9 cancer markers while at the same time, combining major associated symptoms that could lead to pancreatic cancer for the early diagnosis of pancreatic cancer with a high mortality rate, and by using Bayesian conditional probability herewith, they have found a method to diagnose pancreatic cancer at an earlier time.

As a relative prior art, there is a Pancreatic Cancer Composition and Method for Diagnosing Pancreatic Cancer Using the Same disclosed in Korean Patent Publication No. 10-2016-0057352 (published on May 23, 2016).

SUMMARY OF THE INVENTION

The present disclosure is directed to providing a method of providing information for the diagnosis of pancreatic cancer using Bayesian network based on artificial intelligence, a computer program, and a computer-readable recording media using the same.

The objects of the present invention are not limited to the aforementioned object(s), and other objects, which are not mentioned above, will be apparent to a person having ordinary skill in the art from the following description.

According to the present invention, it is possible to provide a method of providing information necessary for diagnosing pancreatic cancer using an artificial intelligence-based Bayesian network of the present invention, including: generating a statistical report by learning medical information of a pancreatic cancer patient; constructing a conditional probability table using statistics for each symptom of an actual pancreatic cancer patient; constructing a Bayesian network using the conditional probability table constructed using the statistics for each symptom; applying a Bayesian conditional probability to the Bayesian network; and deriving a probability of getting pancreatic cancer when there is a specific symptom from the pancreatic cancer patient.

According to a preferred embodiment of the present invention, medical information from a patient with pancreatic cancer may be statistical data acquired through artificial intelligence or machine learning.

In addition, according to a preferred embodiment of the present invention, the statistical data may be a probability of developing pancreatic cancer for at least one item of, abdominal pain, nausea and vomiting, weight loss, jaundice, acute diabetes, CA 19-9 cancer marker, smoking status, family history, male and female.

According to a preferred embodiment of the present invention, the step of constructing the conditional probability table based on statistics of each symptom of an actual pancreatic cancer patient may comprise constructing a conditional probability table for the at least one item of the above-mentioned statistical data, from a statistical report obtained by an actual pancreatic cancer patient.

In addition, according to a preferred embodiment of the present invention, the step of applying the Bayesian conditional probability may be a step of calculating P(P|S) which is a probability of having pancreatic cancer when pancreatic cancer-related symptoms appear, using a Bayesian conditional probability formula, when the probability of a person getting pancreatic cancer is F(S), and a probability of certain symptoms occurring when a person has pancreatic cancer is P(S|P), where P indicates Pancreatic Cancer, and S indicates Symptoms.

According to a preferred embodiment of the present invention, the Bayesian conditional probability formula may be defined by (i) when the event P (P) is true, a conditional probability that P (S) will occur is defined by the following Equation 1, (ii) conversely, a conditional probability that P (P) will occur when P (S) is given is defined by the following Equation 2, (iii) here, P(S∩P)=P(P∩S) is satisfied, and the Equation 2 can be organized to be expressed as the following Equation 3, (iv) thus, a probability of a pancreatic cancer P(P|S) is calculated by the following Equation 4, $$P(S \cap P) = P(S \mid P)P(P) \qquad \text{[Equation 1]}$$

$$P(P \cap S) = P(P \mid S)P(S) \qquad \text{[Equation 2]}$$

$$P(P \mid S)P(S) = P(S \mid P)P(P) \qquad \text{[Equation 3]}$$

$$P(P \mid S) = \frac{P(S \mid P)P(P)}{P(S)}. \qquad \text{[Equation 4]}$$

Other details of preferred embodiments of the present invention are included in the detailed description and the accompanying drawings.

The advantages and/or features of the present invention and the manner of achieving them will be apparent from and elucidated with reference to the embodiments described hereinafter with reference to the accompanying drawings.

However, it should be understood that the present invention is not limited to the embodiments described below, but may be embodied in many different forms and should not be construed as limited to the embodiments set forth herein. And it should be understood that the invention is only defined by the scope of the respective claims.

According to the present invention, a method for providing information for diagnosing pancreatic cancer, a computer program, and a computer-readable recording medium using the artificial intelligence-based Bayesian network can be provided.

According to the present invention, the probability of pancreatic cancer can be calculated quickly and accurately.

In addition, according to the present invention, it is possible to diagnose pancreatic cancer accurately by calculating the probability of accurate pancreatic cancer while allowing early diagnosis by eliminating positive error of CA 19-9 cancer marker.

DETAILED DESCRIPTION OF THE INVENTION

Hereinafter, an exemplary embodiment of the present invention will be described in detail with reference to accompanying drawings.

Also, in the following description of the present invention, a detailed description of a configuration that is considered to unnecessarily obscure the gist of the present invention, for example, a known technology including the prior art, may be omitted.

In addition, in this specification, the same reference numerals are used for the respective constituent elements of the drawings.

Further, in each step described in this specification, an identification number (for example, each reference numeral) is only used for convenience of explanation, and these identification numbers are not intended to definitively designate the order of each step, and unless the specific order of each step is explicitly stated in the context, the order of each step described in the present specification may be different.

Each embodiment of the present invention described below can be modified into various other forms, and the scope of the present invention is not limited to the embodiments described below.

It is also to be understood that each embodiment of the present invention is provided to enable a more general description of the present invention to be more fully understood by those of ordinary skill in the art.

Figure 1:
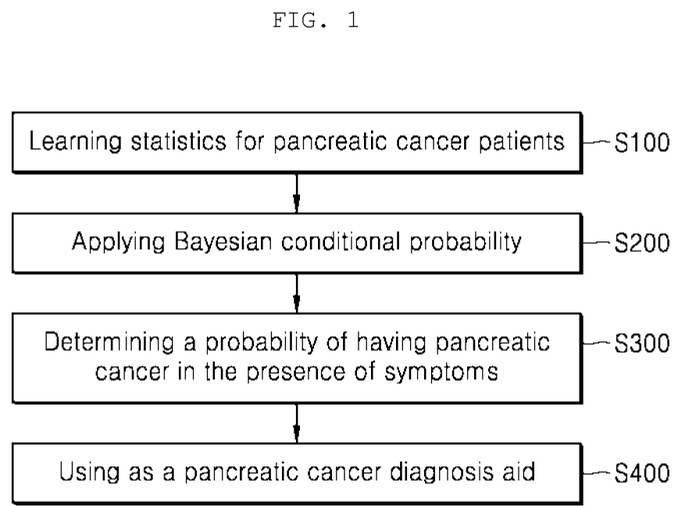
FIG. 1 is a flowchart illustrating an overall method of providing information necessary for diagnosis of pancreatic cancer using artificial intelligence based Bayesian network according to an exemplary embodiment of the present invention.

FIG. 1 is a flowchart illustrating an overall method of providing information necessary for diagnosis of pancreatic cancer using artificial intelligence based Bayesian network according to an embodiment of the present invention.

According to FIG. 1, a method for providing information necessary for diagnosing pancreatic cancer using the artificial intelligence-based Bayesian network of the present invention may include learning statistical data for a pancreatic cancer patient in step S100, applying a Bayesian conditional probability in step S200, deriving a probability of engaging in pancreatic cancer in step S300, and using a diagnosis aid for pancreatic cancer optionally in step S400.

Here, the Bayesian conditional probability as a concept used in the present invention will be briefly described.

When the probability of a person getting pancreatic cancer is P(S) and a probability that a specific symptom will occur when a person has pancreatic cancer is P(S|P), when a Bayesian conditional probability formula is used, conversely, the probability of a having pancreatic cancer when pancreatic cancer-related symptoms appear which is P(P|S), can be calculated. Here, P indicates pancreatic cancer, and S indicates symptoms.

More specifically, the Bayesian conditional probability can be determined through the following steps.

A conditional probability that P (S) occurs when event P (P) is true can be expressed according to a Bayesian conditional probability formula as follows.

$$P(S \cap P) = P(S|P)P(P) \quad \text{[Equation 1]}$$

Conversely, given P(S), a conditional probability that P (P) will occur is as follows.

$$P(P \cap S) = P(P|S)P(S) \quad \text{[Equation 2]}$$

Here, since the relationship of $P(S \cap P) = P(P \cap S)$ is satisfied, the Equation 2 can be organized to be expressed as the following Equation 3.

$$P(P|S)P(S) = P(S|P)P(P) \quad \text{[Equation 3]}$$

Thus, a probability of a pancreatic cancer P(P|S) can be expressed as follows.

$$P(P|S) = \frac{P(S|P)P(P)}{P(S)} \quad \text{[Equation 4]}$$

As indicated above, if P(P) and P(S|P) are known statistically, that is if these values are known in advance, P(P|S) can be calculated later.

In other words, if the probability of a person getting pancreatic cancer and the possibility of showing a specific symptom when a person gets pancreatic cancer is known, then the probability of the person getting pancreatic cancer can be calculated through the actual symptom shown.

Hereinafter, a method for providing information necessary for diagnosing pancreatic cancer using the artificial intelligence-based Bayesian network of the present invention will be described with the Bayesian conditional probability above.

As described above, if it is statistically known in advance that the probability of P(P) and P(S|P), the probability of a general person getting cancer of the pancreas and the specific symptoms of the cancer of the pancreas, it can be seen that the probability of taking pancreatic cancer later (P|S) can be obtained.

In view of the above, the present invention includes learning statistical data on pancreatic cancer patients in step S100.

The present step S100 may be, for example, a step of learning disclosed statistical data related to the pancreatic cancer patients.

In this step S100, it is preferable to use a data collecting device such as a web crawler and perform artificial intelligence such as a neural network or other machine learning to acquire related statistical data and generate a statistical report.

Alternatively, statistical data manually entered in the literature related to cancer diseases may be learned.

The learning of such statistical data can use an artificial intelligence system or a machine learning system, and a detailed system configuration for this purpose is beyond the scope of the present invention, so a detailed description thereof will be omitted.

Hereinafter, statistical reports of the statistical data learned in the step S100 of learning the statistical data of the pancreatic cancer patient of the present invention are summarized in the following Table 1.

TABLE 1

| ITEM | | TRUE 11/Hundred thousand (0.011%)[1] | FALSE 99.98% |
|---|---|---|---|
| Probability of pancreatic cancer | | | |
| Pancreatic cancer patients(PC = TRUE) | Abdominal pain | 41.7%[2] | 58.3% |
| | Nausea and vomiting | 9.1%[2] | 90.9% |
| | Weight loss | 22%[2] | 78% |
| | Jaundice | 6.8%[2] | 93.2% |
| | Newly onset diabetes | 28.0%[2] | 72% |
| | Male | 80.3%[2] | 19.7% |
| | Female | 26%[2] | 74% |
| | CA19-9 numerical positive | 84%[3] | 16% |
| | Smoking rate | 33%[1] | 67% |
| | Family history of PC | 10%[1] | 90% |

[1]: Results from the 2016 statistics of the National Cancer Information Center, Korea.

[2]: Results from the statistical data of 236 people from 2009 to 2014 at Peking Union Medical College, Beijing, China.

[3]: Results from the 2015 statistics of Seoul National University Dept. Hemato Oncology, Korea.

In the step S100 of learning the statistical data on the pancreatic cancer patient of the present invention, the statistical data learned, as shown in Table 1, is the probability of having pancreatic cancer (TRUE) and the probability of not having the same (FALSE), for each item such as irregular abdominal pain, nausea and vomiting, weight loss, jaundice, acute diabetes, CA 19-9, cancer marker, smoking status, and family history, and so on.

In addition, ancillary statistical data such as the probability of pancreatic cancer in men and women can also be studied and provided as statistical reports.

Of course, in the present invention, it should be noted that not only the respective items shown in Table 1 are learned to provide statistical reports, but also other items that help diagnose pancreatic cancer, such as bilirubin or albumin levels, cholangitis and biliary obstruction may be added.

It can be known from Table 1, for example, statistical data showing that the probability of having pancreatic cancer (TRUE) in the case of patients with irregular abdominal is 41.7% (and therefore the probability of not having pancreatic cancer being 58.3%) as a conditional probability, or statistical data showing that the probability of having pancreatic cancer in the case of patients with nausea and vomiting is 9.1% as a conditional probability, and so on.

In addition, Table 1 also shows the probability of pancreatic cancer with a conditional probability of 84% for CA 19-9 cancer markers, but as described above, since a False-Positive occurs it is never desirable to use it as the only standard for diagnosing pancreatic cancer because it may lead to unnecessary surgery or chemotherapy or non-treatment to worsen pancreatic cancer.

Accordingly, in order to use the Bayesian network technique, the inventors of the present invention created a Conditional Probability Table (CPT) for each item in Table 1 to express the probability of each node for determining whether pancreatic cancer is present or not.

That is, according to an exemplary embodiment of the present invention, Bayesian conditional probability application may be performed in step S200.

In this step S200, for example, a method of obtaining the Bayesian conditional probability described above can be applied to the Bayesian network constructed using the conditional probability table of the present invention.

Specifically, in the Bayesian network, the probability of each node is expressed using a conditional probability table. In the present invention, a conditional probability table for each item is created as shown in Tables 2 to 10 below.

Firstly, since a probability can be a node for deciding whether a pancreatic cancer is present or not, as shown in Table 1, it assumed that the pancreatic cancer is a disease that 11 out of 100,000 people develop. And the probability of deciding the presence or absence of pancreatic cancer can be represented as shown in Table 2 below.

TABLE 2

| Pancreatic cancer | P(Pancreatic cancer) |
|---|---|
| T | 0.011% |
| F | 99.98% |

Next, from the statistical data of each symptom in the case of pancreatic cancer patients, the conditional probability of the node related to the irregular abdominal pain symptom can be expressed as shown in Table 3 below.

In pancreatic cancer patients, the probability of having the symptoms is 41.7%, and the probability of not having the symptoms is 58.3%. For convenience, when the patient is not a pancreatic cancer patient, the probability of having the symptoms is 0.1% and the probability of not having the symptoms is 99.9%.

TABLE 3

| Pancreatic cancer | Abdominal pain | P(Abdominal pain \| Pancreatic cancer) |
|---|---|---|
| T | T | 41.7% |
| T | F | 58.3% |
| F | T | 0.1% |
| F | F | 99.9% |

In an equivalent manner as in Table 3, Table 1 shows the conditional probability for each item of statistical data for each symptom in the case of pancreatic cancer patients.

In some cases, even if the patient is not a pancreatic cancer, the probability that the symptom will occur is set at 0.1%, the probability that the symptom will not occur is set at 99.9%, and in some cases a different probability is set.

TABLE 4

| Pancreatic cancer | Nausea Vomitting | P(Nausea Vomitting \| Pancreatic cancer) |
|---|---|---|
| T | T | 9.1% |
| T | F | 90.9% |
| F | T | 0.1% |
| F | F | 99.9% |

TABLE 5

| Pancreatic cancer | Jaundice | P(Jaundice \| Pancreatic cancer) |
|---|---|---|
| T | T | 6.8% |
| T | F | 93.2% |
| F | T | 0.1% |
| F | F | 99.9% |

TABLE 6

| Pancreatic cancer | Weight loss | P(Weight loss \| Pancreatic cancer) |
|---|---|---|
| T | T | 22% |
| T | F | 78% |
| F | T | 0.1% |
| F | F | 99.9% |

TABLE 7

| Pancreatic cancer | CA19-9 | P(CA19-9 \| Pancreatic cancer) |
|---|---|---|
| T | T | 84% |
| T | F | 16% |
| F | T | 0.1% |
| F | F | 99.9% |

TABLE 8

| Pancreatic cancer | Sex(Male) | P(Sex(Male) \| Pancreatic cancer) |
|---|---|---|
| T | T | 80.3% |
| T | F | 19.7% |
| F | T | 50% |
| F | F | 50% |

TABLE 9

| Pancreatic cancer | Smoking | P(Smoking \| Pancreatic cancer) |
|---|---|---|
| T | T | 33% |
| T | F | 67% |
| F | T | 20% |
| F | F | 80% |

TABLE 10

| Pancreatic cancer | Family History | P(Family History \| Pancreatic cancer) |
|---|---|---|
| T | T | 10% |
| T | F | 90% |
| F | T | 0.1% |
| F | F | 99.9% |

Based on the conditional probability for each item of statistical data for each symptom in the case of pancreatic cancer patients shown in the above Tables 3 to 10, it is possible to construct a Bayesian network. By using this Bayesian network, diagnosis of pancreatic cancer is possible from a medical reasoning, such as the probability of developing pancreatic cancer.

Here, reasoning can be broadly divided into diagnosis and causation. Diagnosis refers to describing the cause of a symptom, and causation refers to clarifying the effect when a cause is given.

For example, the process of identifying the presence of pancreatic cancer by looking at specific clinical symptoms can be referred to as a diagnosis, and on the other hand, the process of identifying symptoms that may be seen in patients already having pancreatic cancer can be referred to as causation.

In the present invention, the Bayesian network was used to deduce (i.e. diagnose) the probability of a person having pancreatic cancer using statistics (i.e. causation) obtained from the symptoms of pancreatic cancer patients.

Specifically, according to the present invention, the Bayesian network can display the knowledge of a specific situation in the form of cause and effect.

At this time, the Bayesian network displays nodes corresponding to the propositions as nodes (ellipse), gives a name representing the proposition, and draws an edge from the proposition of the cause to the proposition of the effect.

Thus, connecting both the cause and the effect finally completes the Bayesian network.

In this case, when connecting the cause and the effect, they must be connected only in one direction, and the graph connected in only one direction is referred to as a directed acyclic graph.

Figure 2:
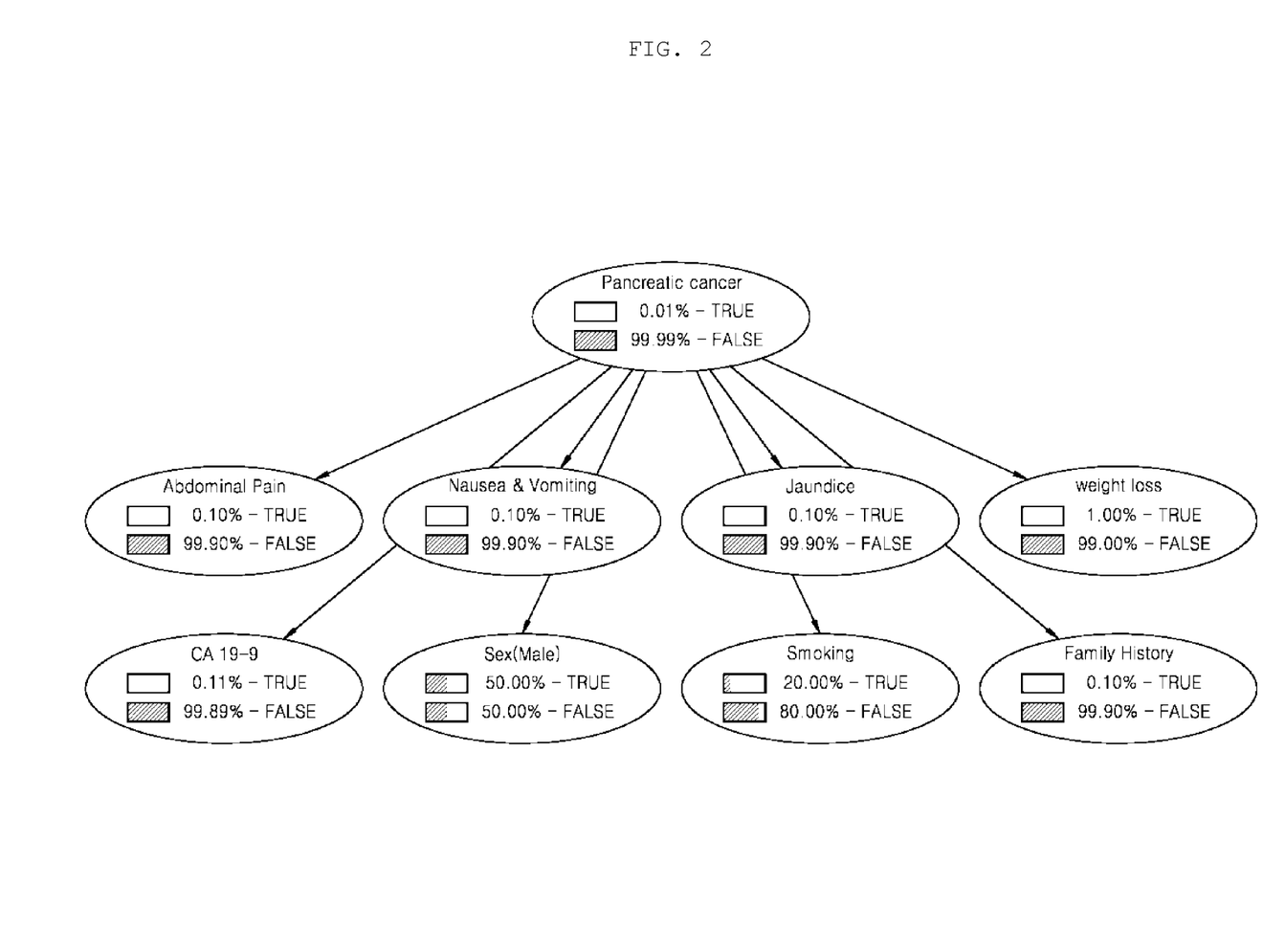
FIG. 2 shows an example embodiment of the present invention, and is a diagram showing a Bayesian network.

According to one embodiment of the present invention, the diagnostic probability of pancreatic cancer using the statistics of Tables 3 to 10 is shown in FIG. 2 as a Bayesian network graph.

FIG. 2 shows a preferred embodiment of the present invention, and is a diagram showing a Bayesian network.

In this case, when the number of cases is small, that is, when the number of nodes is not large, it is possible to proceed sufficiently manually. However, if the number of nodes increases, the amount of computation increases rapidly. Therefore the inventors of the present invention use SamIam (UCLA, USA) package, which is open software. In order to construct the Bayesian network, each node is configured as shown in FIG. 2, and the desired effect is derived by executing the program.

In FIG. 2, in view of the symptoms (i.e. an effect) of patients with pancreatic cancer (i.e. a cause), each of these causes and effects is indicated on each node by a prior probability (i.e. preliminary limit probability).

As can be seen from FIG. 2, for example, the symptom of irregular abdominal pain is indicated by the probability of 0.10% of pancreatic cancer and the probability of not being 99.90% of pancreatic cancer.

It is preferable to confirm from the statistical report obtained in the case of a pancreatic cancer patient, that is, a statistical report obtained at a probability of 100%, whether or not the prior probabilities of the cause and the effect shown in each node shown in FIG. 2 coincide with each other. The probability value at this time is called the posterior limit probability.

A method for confirming the posterior limit probability will be described with reference to the graph of FIG. 3.

Figure 3:
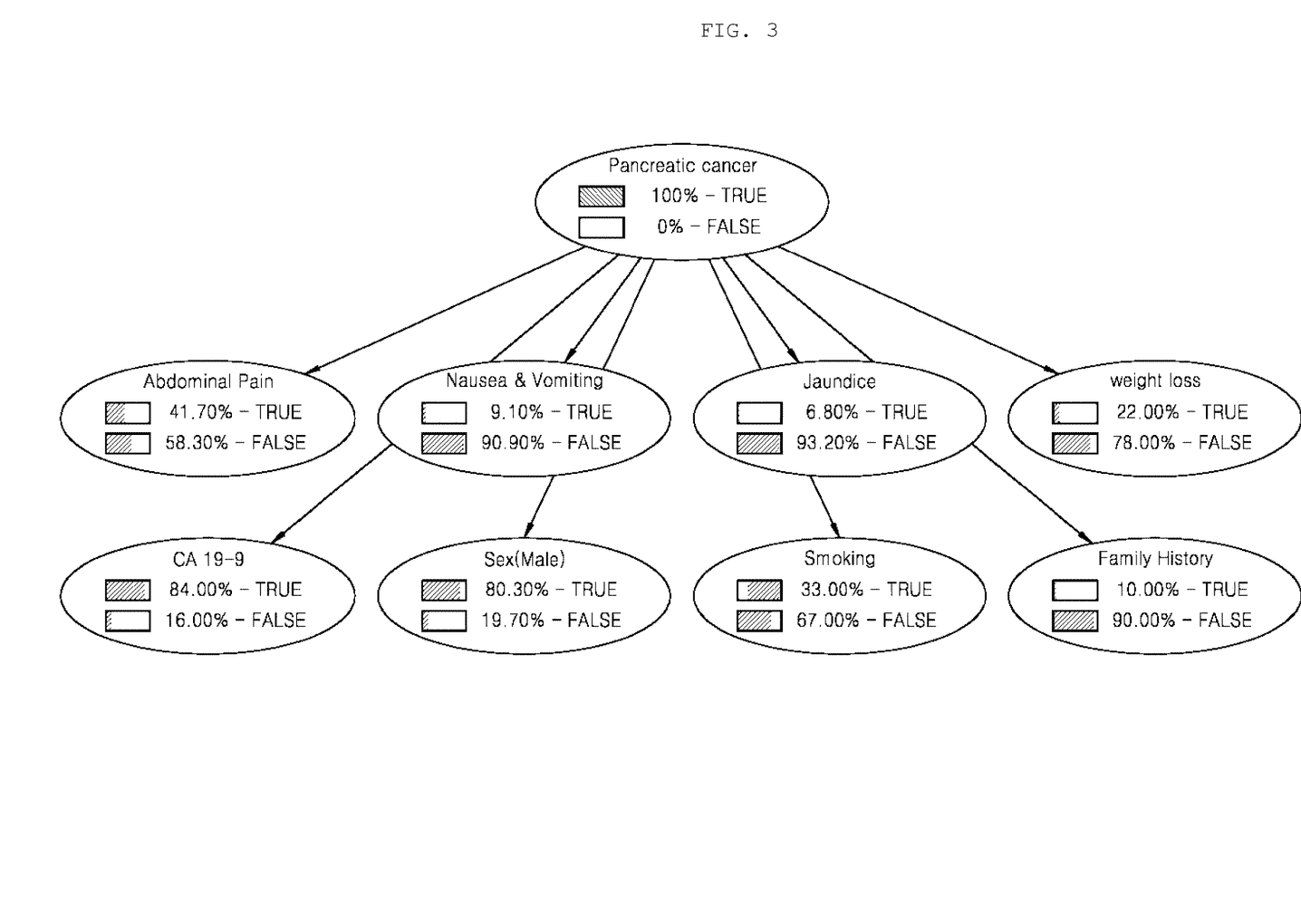
FIG. 3 shows an example embodiment of the present invention, and is a diagram illustrating a method of confirming a posterior limit probability.

FIG. 3 shows a preferred embodiment of the present invention, and shows a method of confirming the posterior limit probability.

It can be seen from FIG. 3 that the probability of a pancreatic cancer in the case of actual pancreatic cancer patients (i.e., 100% probability) and irregular abdominal pain is 41.70%, and 9.10% in cases of nausea and vomiting.

In summary, it should be noted that the graph shown in FIG. 3 is a representation of the contents shown in Table 1 as a Bayesian network.

Next, a step S300 of deriving the probability of getting pancreatic cancer may be performed when symptoms are present. This step S300 is a step of deriving the probability of the patient getting pancreatic cancer or already having pancreatic cancer from the clinical symptoms of each patient based on the Bayesian conditional probability obtained by the Bayesian conditional probability application step S200.

A preferred embodiment of this step S300 will be described with reference to FIG. 4.

Figure 4:
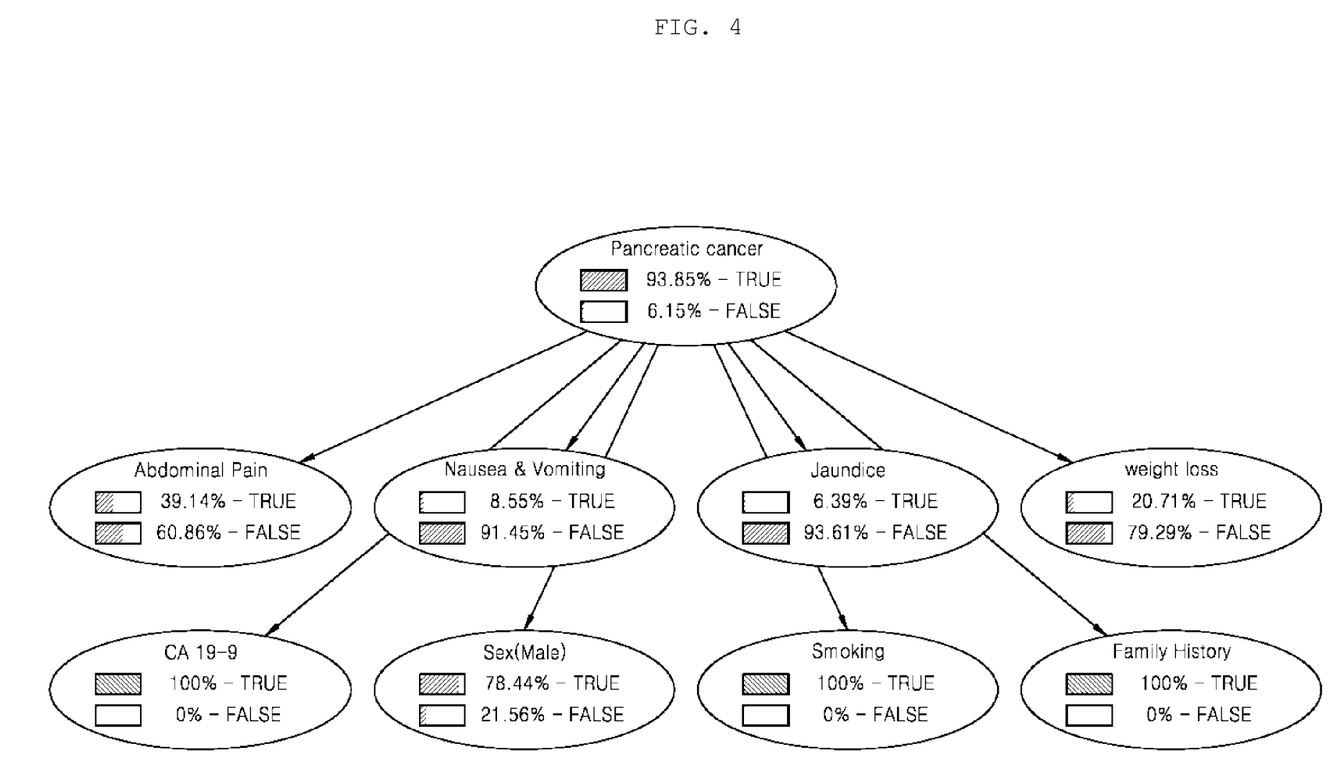
FIG. 4 shows an example embodiment of the present invention, and is a diagram illustrating a method for deriving a probability of a patient getting pancreatic cancer or already having pancreatic cancer from clinical symptoms of each patient based on Bayesian conditional probability.

FIG. 4 shows a preferred embodiment of the present invention, it is a diagram showing a method of deriving a probability of a patient getting pancreatic cancer or already having pancreatic cancer based on the clinical symptoms of each patient based on Bayesian conditional probability.

According to FIG. 4, when there is a family history of pancreatic cancer (i.e. a probability of 100%), the CA 19-9 cancer marker level is positive (i.e. 100% probability), and the probability of having pancreatic cancer is 93.85%.

At this time, it is well known that the value of the CA 19-9 cancer marker is preferably 37 U/ml or less in the case of a conventional art.

Based on the above explanation, Table 11 summarizes the case of diagnosing the possibility of pancreatic cancer when the individual is manifested by each symptom.

TABLE 11

| SYMPTOM | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| ABDOMINAL PAIN | ⊙ | | | | | | | | ⊙ | | | | ⊙ | | | |
| NAUSEA & VOMITING | | ⊙ | | | | | | | ⊙ | ⊙ | | | | ⊙ | | |
| JAUNDICE | | | ⊙ | | | | | | | ⊙ | ⊙ | | | | ⊙ | |
| WEIGHT LOSS | | | | ⊙ | | | | | | | ⊙ | ⊙ | | | | |
| CA19-9 | | | | | ⊙ | | | | | | | ⊙ | ⊙ | ⊙ | ⊙ | ⊙ |
| SEX(MALE) | | | | | | ⊙ | | | | | | | | | | |
| SMOKING | | | | | | | ⊙ | | | | | | | | | |
| FAMILY HISTORY | | | | | | | | ⊙ | | | | | | | | ⊙ |
| PROB. PC(%) | 4.39 | 0.99 | 0.74 | 2.36 | 8.46 | 0.02 | 0.02 | 1.09 | 80.67 | 40.5 | 62.2 | 95.31 | 97.47 | 89.37 | 86.27 | 90.24 |

⊙ = TRUE

As what can be known from Table 11, the probability of a pancreatic cancer when the abdominal pain is True as a single symptom without any other symptoms is 4.39%, the possibility of pancreatic cancer when nausea and vomiting is True is 0.99% and so on.

In addition, it can be seen that two symptoms occur simultaneously, for example, when irregular abdominal pain and nausea & vomiting are simultaneously true, the possibility is 80.67%, and when nausea & vomiting and jaundice are simultaneously true, the possibility is 40.5%.

Thus, from Table 11 we can know that when calculating the probability of a pancreatic cancer only by a single symptom, a low probability from which a meaningful effect cannot be calculated, is derived, and when at least two major symptoms are manifested, there is a high probability, for example, a probability of 50%, that a probability indicating the possibility of pancreatic cancer is derived.

The most notable point here is that when only CA 19-9 alone is true, there is a probability of 8.46% of having pancreatic cancer, but when CA 19-9 and abdominal pain are True at the same time, a high value of 97.47% is shown. It should be noted that this shows a large difference from 8.46% and 4.39% when each case alone is True.

In other words, in the case of CA 19-9 and other main symptoms being True simultaneously, it shows high probability about 90% (In Table 11, wherein SYMPTOM numbers 12, 13, 14, 15, and 16, probabilities of 95.31%, 97.47%, 89.37%, 86.27%, and 90.24%). This seems to reflect the characteristic of the conditional probability of the Bayesian network of the present invention, therefore, it is expected that doctors will be an important function for early selection of candidates for pancreatic cancer.

Finally, the step of S400 of utilizing the probability of developing pancreatic cancer, obtained by the method of providing information necessary for diagnosis of pancreatic cancer using the artificial intelligence-based Bayesian network according to the present invention, as an aid for diagnosis of pancreatic cancer, may be selectively performed.

In this step S400, the doctor selects and uses the probability as an aid for diagnosis of pancreatic cancer.

While the present invention has been particularly shown and described with reference to exemplary embodiments thereof, it is evident that many alternatives, modifications and variations will be apparent to those skilled in the art. It will be understood by those skilled in the art that various changes in form and details may be made therein without departing from the spirit and scope of the invention as defined by the appended claims.

In addition, since the present invention can be embodied in various forms, and should not be construed as being limited to the embodiments set forth herein. Rather, these embodiments are provided so that this disclosure will be thorough and complete and will fully convey the concept of the invention to those skilled in the art, and the present disclosure will only be defined by the appended claims.

What is claimed is:

1. A method of providing information for a diagnosis of pancreatic cancer using Bayesian network based on artificial intelligence, the method comprising:
   generating a statistical report by learning medical information of a patient with pancreatic cancer, wherein the medical information is configured to have a probability of developing pancreatic cancer for at least one item of, abdominal pain, nausea and vomiting, weight loss, jaundice, acute diabetes, CA 19-9 cancer marker, smoking status, family history, male and female, which is statistical data obtained through artificial intelligence or machine learning;
   constructing a conditional probability table using statistics for each symptom of an actual pancreatic cancer patient;
   constructing a Bayesian network using the conditional probability table constructed using the statistics for each symptom;
   applying a Bayesian conditional probability to the Bayesian network; and
   deriving a probability of getting pancreatic cancer when a specific symptom is present from the pancreatic cancer patient,
   wherein the Bayesian network is a graph which expresses knowledge of a specific situation in a form of cause and effect, displaying what corresponds to a proposition as an elliptical node, gives a name representing the proposition, and is a directed acyclic graph wherein an edge is drawn from a proposition being the cause to a proposition being the effect so both the cause and the effect are connected in only one direction.

2. The method of claim 1, wherein the step of constructing a conditional probability table using statistics for each symptom of an actual pancreatic cancer patient comprises, constructing a conditional probability table for the at least one item of the statistical data, from a statistical report obtained for an actual pancreatic cancer patient.

3. The method of claim 1, wherein the step of applying a Bayesian conditional probability is a step of calculating P(P|S) which is a probability of having pancreatic cancer when pancreatic cancer-related symptoms appear, using a Bayesian conditional probability formula, when a probability of a person getting pancreatic cancer is P(S), and a probability of certain symptoms occurring when a person has pancreatic cancer is P(S|P), where,
   P: Pancreatic Cancer,
   S: Symptoms.

4. The method of claim 3, wherein the Bayesian conditional probability formula is,
  (i) when event P(P) is true, a conditional probability that P(S) will occur is defined by a following Equation 1,
  (ii) conversely, the conditional probability that P(P) will occur when P(S) is given is defined by a following Equation 2,
  (iii) here, a relationship of P(S∩P)=P(P∩S) is satisfied, and the Equation 2 can be organized to be expressed as a following Equation 3,
  (iv) thus, the probability of a pancreatic cancer P(P|S) is calculated by a following Equation 4, $$P(S \cap P) = P(S \mid P)P(P) \qquad \text{[Equation 1]}$$

$$P(P \cap S) = P(P \mid S)P(S) \qquad \text{[Equation 2]}$$

$$P(P \mid S)P(S) = P(S \mid P)P(P) \qquad \text{[Equation 3]}$$

$$P(P \mid S) = \frac{P(S \mid P)P(P)}{P(S)}. \qquad \text{[Equation 4]}$$

5. A computer-readable recording medium storing a program for implementing the method according to claim 1.

6. A computer program stored on a computer readable medium for implementing the method according to claim 1.

* * * * *